United States Patent [19]
Boardman et al.

[11] Patent Number: 4,808,637
[45] Date of Patent: Feb. 28, 1989

[54] SUPERABSORBENT COMPOSITION AND PROCESS

[75] Inventors: Franklin Boardman, Englishtown; John M. Lesniak, Hazlet, both of N.J.

[73] Assignee: Johnson & Johnson Patient Care, Inc., New Brunswick, N.J.

[21] Appl. No.: 49,877

[22] Filed: May 14, 1987

[51] Int. Cl.$^4$ .............................................. C08J 9/00
[52] U.S. Cl. ................................. 521/50.5; 525/329.7; 525/330.3; 525/360; 525/366; 525/917; 525/918; 528/271; 528/392; 528/395; 528/485; 528/488; 528/499; 528/503
[58] Field of Search ............... 528/271, 392, 395, 485, 528/488, 499, 503; 521/50.5; 525/329.7, 330.3, 360, 366, 917, 918

[56] References Cited

U.S. PATENT DOCUMENTS 4,090,013  5/1978  Ganslaw et al. ............... 525/327.2
4,524,186  6/1985  Nagase ............................ 525/328.8

Primary Examiner—John Kight
Assistant Examiner—S. A. Acquah
Attorney, Agent, or Firm—Joseph J. Brindisi

[57] ABSTRACT

The present invention provides an acrylate superabsorbent composition having an improved rate of absorbency, low residual acid content, and a low acrylate monomer content. Acrylic acid, an alkali metal salt of carbonic acid, aluminum acetate, sodium sulfate and water are uniformly reacted preferably using microwave radiation as the heat source.

20 Claims, No Drawings

SUPERABSORBENT COMPOSITION AND PROCESS

The present invention relates to an improved acrylate superabsorbent composition and is more particularly concerned with an ionically crosslinked poly (alkali metal acrylate), which is subtantially fully neutralized with alkali, and which has a low residual monomer content, and with the process used for making these and other superabsorbents which involves the use of ultra-high frequency radiation, such as microwaves, in a uniform reaction step.

BACKGROUND OF THE INVENTION

A number of years ago "superabsorbent materials", i.e., materials which will absorb many times their weight of liquid were developed. Currently, the superabsorbent materials used in industry are synthetically formed compositions, such as polyacrylates. It is the latter class of compositions derived from acrylic acid to which the present invention pertains.

Polyacrylic acid compositions have been known for some time as is evidenced in the U.S. Pat. No. 2,833,745. This patent teaches preparing the alkali metal or ammonium salt of a polyacrylic acid by mixing the acrylic acid with alkali, or ammonium carbonates, or bicarbonates and then carrying out the polymerization by the addition of accelerators in a completely anhydrous medium or in a small amount of water. The polymerizate obtained is solid and somewhat porous. The solid product is then comminuted to a powder. The resulting polymer product is soluble.

In the series Textile Science and Technology published by Elsevier Science Publishers B.V., in Volume 7, entitled "Absorbency", (©) 1985, Chapter VI discusses the Development of Synthetic Superabsorbent Polymers, including cross-linked polyacrylate superabsorbents, referenced to various patents and other literatures.

The superabsorbent polymeric compositions of the present invention differ from those of the prior art, not in their main monomeric constituents, but in the fact that the acrylic acid monomer is substantially fully neutralized and that the residual monomer level is extremely low.

The presently commercially available superabsorbents contain residual monomer levels as high as 4,000 ppm (parts per million). The industry has been trying to eliminate or at least significantly lower these levels, without substantially increasing the price. Arakawa currently sells a superabsorbent with residual monomer levels of 400 ppm. The Arakawa material is made by a different process than the present invention, and has a different composition in that it is not substantially fully neutralized. As shown by various tests, it and other prior art commercial superabsorbents have lower pH values, and are neutralized to a lesser degree than the superabsorbents of the present invention. By the use of the novel process of the present invention, this industry goal of moving closer to eliminating any monomer residue has been approached when using the most preferred materials, and great improvement has been made even with the less preferred embodiments.

Various different types of absorbent compositions are taught in U.S. Pat. No. 4,043,952, which treats the surface of a water absorbent composition by ionically complexing the surface of the composition. The water absorbent composition is dispersed, with a polyvalent metal cation, in a dispersing medium in which the composition is insoluble. The composition is an anionic polyelectrolyte. The dispersion is maintained at a given temperature for a period of time sufficient to ionically complex the exposed surface of the composition.

In the U.S. Pat. No. 4,090,013 a water-swellable, water-insoluble absorbent composition is prepared which has the ability to uncomplex at an elevated pH and recomplex at a lower pH. Although, as evidenced by the above, the water-swellable, water-insoluble compositions have been treated to improve their characteristics, no single-step process has provided a water-swellable, water-insoluble composition which absorbs water rapidly, has a low monomer content, and a low residual acid content.

Foamed water-swellable polymeric water absorbent materials are taught in Scott et al., U.S. Pat. No. 4,529,739 (assigned to Dow Chemical) including alkali metal salts of homopolymers of acrylic acid and certain copolymers thereof, which are made by contacting a latex dispersion of a polymer with a carbon dioxide yielding decomposeable blowing agent capable of neutralizing pendant moieties (e.g. sodium carbonate and sodium bicarbonate, among others). Applicants process involves some of the same materials, but applicants neutralize a monomer with (bi)carbonates while the Scott et al. process neutralizes a polymer.

Microwave Heating (ultra high frequency) radiation has previously been used for heating and/or drying and even for effecting chemical modification of starch (EPO Pat. No. 0,041,316 to CPC International) but it has not been used for the purpose of the present invention to provide an environment permitting uniform heating and reacting throughout a chemically initiated polymerization reaction, to the best of our knowledge.

SUMMARY OF THE INVENTION

The present invention provides a water-swellable, water-insoluble composition which absorbs water rapidly, has a total residual monomer content of less than about 200 ppm, (said monomer content includes both any residual acrylic acid monomer and any residual alkali metal acrylate monomer). Polyacrylates with a residual monomer content below 35 ppm have been obtained by the practice of our invention.

The present invention provides a superabsorbent composition comprising the product resulting from the process of the present invention, i.e. from uniformly reacting a mixture of acrylic acid, an alkali metal salt of carbonic acid, aluminum acetate, sodium persulfate and water at a temperature of at least 70° C. for at least one minute. The resulting product is an alkali metal polyacrylate having a residual total monomer content from the acrylic acid and/or its alkali metal salt monomers of less than about 200 ppm.

The process of the present invention is the free radical polymerization process for preparing a poly (alkali metal acrylate) using a chemical free-radical initiator, an ionic cross-linking agent, and an alkali metal salt of carbonic acid, which process is carried out in an environment that allows for rapid polymerization whereby there is uniform reacting of the reactants, so that the final product is relatively uniform also. The term "uniformly reacting" means that the reaction is carried out in an environment which enables the reaction to take place virtually simultaneously throughout the reaction mixture. A preferred means for providing such reaction environment is a microwave oven. By subjecting the aqueous mixture to ultra high frequency radiation, e.g. microwaves, to achieve the reaction temperature, the reaction takes place substantially simultaneously throughout the reaction mixture. Any means which will provide an environment whereby the reaction takes place simultaneously throughout the mixture, is a suitable means for use in the present invention.

For practical economic purposes since the process and product of the present invention is intended for industrial use, the poly (alkali metal acrylates) will involve either sodium or potassium as the alkali metals involved. Of the two, significantly better results have been obtained with potassium, in terms of obtaining the lowest residual monomer content. The novel process of the present invention can be used to make poly (sodium acrylate) superabsorbents and poly (potassium acrylate superabsorbents), but only the latter have the very low residual monomer contents.

In one embodiment the present invention provides a water-swellable, water-insoluble superabsorbent composition which is comprised of a reaction product of about 100 parts of acrylic acid by weight (all parts are by weight) sufficient parts of an alkali metal salt of carbonic acid to substantially neutralize the acrylic acid, from about 1 to about 7 parts of aluminum acetate, from about 0.2 to about 2 parts of sodium persulfate, and from about 75 to about 175 parts of water. The above reaction mixture is reacted in a microwave oven to attain a temperature of at least 70° C. for at least 1 minute until reaction is completed. The resulting reaction product is an alkali metal polyacrylate which has a residual monomer content of less than about 200 ppm. Further, the resulting composition is a crosslinked composition which is substantially water-insoluble and provides a high degree of water or liquid absorbency. The product appears as a foam; it need not be pulverized but rather may be used in its foamed condition, which frequently resembles a "pancake" or foamed sheet. The foam may be pulverized or ground to a powder form, if desired for any of the uses to which conventional powdered superabsorbents are put.

The present invention provides a composition which is simply prepared, in substantially a one-step operation, providing not only a water-swellable composition, but a water-insoluble composition having virtually no residual acrylic acid content and a very low residual acrylate monomer content. Residual total monomer contents of below 200 ppm can be obtained practicing the process of this invention. But, the process invention is not limited to producing such low residual monomer content superabsorbents, The use of microwave ovens, i.e. uniform reaction, to make any superabsorbents (even those with a high residual monomer content) is novel, and to be regarded as part of out invention.

MORE DETAILED DESCRIPTION OF THE INVENTION

In carrying out the process of this invention, acrylic acid, in an amount of 100 parts by weight is admixed with an alkali metal salt of carbonic acid in an quantity sufficient to "substantially neutralize" the acrylic acid. A sodium or potassium carbonate or bicarbonate may be used as the carbonic acid salt.

While it is preferred that the quantity of carbonic acid salt used be that stoichiometric amount which will and which actually does neutralize 100% of the acrylic acid in actual practice the neutralization of all the acid COOH groups can be difficult to attain, and to measure in absolute quantitative numbers. By use of the term "substantially neutralize(d)" were require our superabsorbents to be neutralized to a greater extent than prior art commercially available superabsorbents.

For purposes of defining the present invention, we use an indirect titration method to measure and specify exactly when the alkali metal salt of acrylic acid is to be regarded as "substantially neutralized". It is based on the idea that if theoretically the superabsorbent was entirely made of the potassium salt of uncrosslinked polyacrylic acid, it would have a pH of 8.6. Commercially available superabsorbents all require subtantial amounts of a base in order to raise their pH to 8.6. In contrast, the superabsorbents of the present invention, being already substantially neutralized, require much lesser amounts of a base in order to raise their pH to 8.6. The fact that superabsorbents are crosslinked polymers, which are sterically hindered, prevents more exact types of measurements.

The theory and exact steps of the tritration procedure actually used in testing the crosslinked superabsorbents is described in detail, after Example 5. Using that titration procedure, when less than 3.0 milliequivalents of 0.1N potassium hydroxide are required to bring 3.3 grams of alkali metal polyacrylate of the present invention to the pH 8.6 end point, this is to be regarded as "substantially neutralized". As will be seen, the prior art commercial Arasorb (Arakawa) superabsorbent required 7.71 milliequivalents (meq) of KOH, as contrasted to the 1.61, 1.89, and 2.28 meq. of KOH required in three different runs of the superabsorbent of the present invention.

The present process can be conducted in a batch, a semi-continuous or a continuous manner, which is another reason why use of the proper theoretical stoichometric amount of carbonic acid salt will not always result in 100% neutralization.

An ionic crosslinking agent, i.e., aluminum acetate, must be present in the admixture in an amount from about 1 to about 7 parts aluminum acetate for each 100 parts of acrylic acid. Preferably from about 2 to about 4 parts of aluminum acetate by weight are used per 100 parts of acrylic acid by weight. The preferred grade of aluminum acetate is basic aluminum acetate stabilized with boric acid, e.g. that sold by Niacet Corporation, Niagara Falls, N.Y.

Also contained in the admixture is an initiator, i.e., sodium persulfate, which should be present in an amount from about 0.2 to about 2 parts sodium persulfate by weight per 100 parts by weight of acrylic acid. The admixture should also have mixed in about 75 to about 175 parts by weight of water per 100 parts by weight of acrylic acid.

The foregoing admixture is placed in a microwave oven and subjected to the ultra-high frequency radiation for a period of time sufficient for the reaction mixture to reach a temperature of at least 70° C. can be maintained at a temperature of at least 70° C. for at least 1 minute.

Ultra-high frequency radiation otherwise known as microwaves, has a frequency in the range of 300 MHz to 300,000 MHz. Within this range only certain specific bands are permitted for industrial use in many countries. Generally, these include 915, 2,450, 5,800, and 22,155 MHz. In industry in the U.S. it is conventional to use a frequency of about 2,450 MHz. The temperature of the reaction mixture when the mixture is subjected to microwave heating, should reach 70° C. and be held at least at that temperature for at least 1 minute. The microwave oven can be shut off when the reaction has produced the resultant desired product, usually in less than 2 minutes. The resultant product appears in the form of a foamed sheet, or a pancake. The process can be conducted as a batch operation or as a semi-continuous or continuous process. When conducted in a continuous manner, the reaction mixture when formed is dropped onto a conveyor belt which passes through a microwave oven.

The following working examples illustrate specific embodiments of the present invention and it is not intended that the invention be limited in any way.

EXAMPLE 1

Poly(sodium acrylate)

Sodium bicarbonate 16.8 g, aluminum acetate 0.28 g, and potassium persulfate 0.5 g are blended together. To this mix, acrylic acid (available from Aldrich Chemical Company, Milwaukee, Wis./it is inhibited with 200 ppM hydroquinone monomethyl ether) in an amount of 13.7 ml and water in the amount of 10 ml is added. The entire mixture is stirred producing a white slush in which some bubbles appear. The mixture becomes cool as the sodium bicarbonate neutralizes the acrylic acid in an endothermic reaction. The mixture is heated in a Hotpoint Model RF53C microwave oven on the high setting for 2 minutes. The slush is transformed into a white pancake-type product. In this instance, the product is ground to a 20 mesh white powder.

The white powder is tested by taking 0.5 g of the powder and placing it in a tea bag. The tea bag is immersed in a synthetic urine solution and after 10 seconds is removed, the amount of urine absorbed is then calculated. The test is repeated, this time allowing the product to remain immersed for 30 seconds and then a third sample remains immersed for 1.5 minutes. The results of the test paper in Table I below.

TABLE I

| Time | Milliliters Absorbed |
|---|---|
| 10 seconds | 18.3 |
| 30 seconds | 24.2 |
| 90 seconds | 27.5 |

The synthetic urine solution is a solution of 2% urea, 1% sodium chloride, and a trace amount of a phosphate buffer.

The residual monomer level including the combined residual acrylic acid monomer and sodium acrylate monomer is 0.08% or 800 ppm.

EXAMPLE 2

Poly(sodium acrylate)

Following the procedure of Example 1 and using the same materials, except before being heated in the Hotpoint Moel RF53C microwave oven, a free radical crosslinking agent, diallyl tartaramide, is added in the amount of 0.25 g to the mixture and then blended with the acrylic acid and water. The mixture is treated for 2 minutes at high microwave heating. The resulting polymer provides the following absorbency values:

TABLE 2

| Time | Milliliters Absorbed |
|---|---|
| 10 seconds | 19.5 |
| 30 seconds | 21.2 |
| 90 seconds | 22 |

The total residual acrylic acid and acrylate monomer level is about 200 ppm. In this test, the pancake-like substance obtained from the reaction is not ground into a powder, but is tested using the same tea bag test. The absorbencies of the unground sample are substantially the same as those which were ground to a 20 mesh powder In this example a free radical covalent crosslinking agent, diallyl tartaramide, is used, in addition to the ionic cross-linking agent, which serves to lower the total acrylic acid monomer and acrylate monomer level to about 200 ppm. Without the free radical agent the residual monomer level would have been 800 ppm.

EXAMPLE 3

Poly(Potassium acrylate)

To a 400 milliliter beaker equipped with a magnetic stirring bar, is added 11 milliliters of water. Sodium persulfate, in an amount of 0.2 g, and potassium carbonate, in the amount of 13.8 g, are added and stirred for 2 minutes. Aluminum acetate, in the amount of 0.28 g, is added and the mixture is mixed for 90 seconds. Acrylic acid in the amount of 13.7 milliliters is added over a 6 to 3 minute period. If necessary, the stirring rate is increased to prevent premature polymerization. After stirring is completed, and preferably any foam which is formed has ceased forming, the mixture is subjected to Hotpoint microwave heat at the high cycle for 75 seconds. The results of the tea bag test on the sample prepared are as follows:

TABLE 3

| Time | Milliliters per Gram |
|---|---|
| 10 seconds | 24 |
| 30 seconds | 37 |
| 60 seconds | 40 |

The total acrylic acid residual monomer plus potassium acrylate monomer level is about 32 ppm.

EXAMPLE 4

Poly(Potassium Acrylate)

To a solution of potassium carbonate, 13.8 g in 11 milliliters of water is added; aluminum acetate, in the amount of 0.28 g, is then added with stirring. A stream of acrylic acid, 13.7 milliliters in all, in 5 milliliters of water, is added with stirring causing evolution of carbon dioxide gas. When the addition is complete, potassium persulfate in the amount of 0.2 g is introduced to the mixture while stirring continues. The mixture is subjected to microwave cooking for 1 minute at a high cycle. The tea bag test using synthetic urine produces the following results.

TABLE 4

| Time | Milliliters per Gram |
|---|---|
| 10 seconds | 17.3 |
| 30 seconds | 26.2 |
| 60 seconds | 31.1 |

The resulting potassium polyacrylate composition has minimally detectable levels of residual monomer i.e. of potassium acrylate or acrylic acid monomer.

In carrying out the process of this example, potassium persulfate may be replaced by either sodium persulfate or ammonium persulfate. Sodium persulfate is preferred because of its higher solubility in water and because there is no possibility of generating ammonia fumes as when using ammonium persulfate.

The reagents, excluding acrylic acid, can all be introduced into a reaction vessel as separate saturated aqueous solutions and need not be introduced as solids. The acrylic acid is generally best introduced as the pure liquid. It may be diluted up to about 10% by water.

As can be seen from the examples above, it is not necessary to use a covalent crosslinking agent. The composition as produced in accordance with the present invention generally has less than 20% extractables in water.

The optimal reaction environment is that which will provide heat throughout the reaction mixture simultaneously, thus decomposing all of the persulfate quickly to obtain the free radicals for polymerizing all of the acrylic acid. If too much heat is applied rapidly, the water is driven off and the polymerization is incomplete, resulting in high monomer levels. If too little heat is applied the sodium persulfate does not decompose rapidly and again the polymerization is incomplete.

EXAMPLE 5

Continuous Process—Poly (Potassium Acrylate)

In this example acrylic acid is mixed with water, an amount of potassium carbonate calculated to effect 100% neutralization of the acrylic acid, aluminum acetate, and sodium persulfate, using a TwinFlow CVR Meter, Mix, and Dispense machine manufactured by Liquid Control Corporation, North Canton, Ohio.

Cylinder A of this machine was filled with glacial acrylic acid stabilized with 200 ppm hydroquinone monomethyl ether obtained from Aldrich Chemical Company, Milwaukee, Wis.

Cylinder B of this machine was filled with an aqueous solution prepared in the following manner:

To 200 ml of water were stirred in 28.6 g basic aluminum acetate, stabilized with boric acid (Niacet Cor., Niagara Fall, N.Y.). After the aluminum acetate dissolved, 20 g sodium persulfate (FMC Corp., Industrial Chemicals Group, Philadelphia, Pa.) were added and stirred until solution again took place. This new solution was then poured into 2000 ml of stirred 47% potassium carbonate in water (Textile Chemical Co., New Brunswick, N.J.). The final solution was poured into Cylinder B.

Piston pumps connected to cylinders A and B ejected their contents, forcing both chemicals into a static mixer. Out of the static mixer came a white froth; the foaming caused by carbon dioxide gas evolved by the reaction of acrylic acid with potassium carbonate. The froth was ejected in 20 gram shots at the rate of 30 shots per minute.

The froth was deposited onto a Teflon belt of a Thermex Model 5015, 15 kw Conveyorized Microwave Oven, manufactured by Thermex/Thermatron Inc., Bay Shore, N.Y. The belt ran at 10 feet per minute and 10 kw of energy powered four microwave guns in the oven. Each shot was carried through the oven for one minute; the froth had been converted to a flexible solid foam by the time it emerged from the other end of the oven. The foam was pulled off the Teflon belt and could be wound up. (When emerging from the oven the foam is hot and flexible, on cooling the flexibility diminishes).

The foam, on removal from the oven, was cut into pieces and characterized as to absorbency and residual monomer levels with no additional processing. The results obtained were:

CHARACTERIZATION

Teabag Absorbency

Approximately 0.3 g of poly(potassium acrylate) was placed in a Tetley teabag which had been slit open and emptied of tea. The bag was stapled and dipped in 0.85% saline solution (Allied Chemical, Fisher Scientific, Orangeburg, N.Y. 10962) for 10 seconds, then 20 additional seconds, and then 30 additional seconds. After each dip the increase in weight of the teabag was recorded to give absorbency values for 10 seconds, 30 seconds, and 60 seconds respectively. The teabag was then squeezed by hand until the bag recorded absorbencies:

| Seconds | ml Saline/g. Polymer |
|---|---|
| 10 | 16 |
| 30 | 29 |
| 60 | 36 |
| "Squeeze" | 20 |

Residual Monomer Levels: Total Acrylic Acid from both free Acrylic Acid and Acidified Potassium Acrylate: 36, 37 ppm (for duplicate analysis).

The polymers prepared by this Example 5 were analyzed for residual acrylic acid by high performance liquid chromatography, (HPLC), the method presently considered state of the art. [The polymers of Examples 1-4 were originally characterized by gas chromatographic analysis for acrylic acid. However, since HPLC is considered more accurate, the results shown in Examples 1-4 were adjusted upwards to agree with our correlation of the two procedures, as based on a common polymer sample which had been analyzed by both methods.]

The polymers prepared by Example 5 were also analyzed for degree of neutralization by the following titration method.

THE TITRATION OF CROSSLINKED POTASSIUM POLYACRYLATE

The potassium salt of polyacrylic acid (KPAA) was titrated as a suspension to determine the base required to reach the titration end point. The titration was carried out in 0.15M potassium chloride to reduce the swelling of the polymer and to buffer the ionic strength of the mixture. The polymer was dried at 105° C. for 18 hours and ground into granules using a mortar and pestle. KPAA was found to contain 70% residue upon dry ashing indicating an organic content of 30%. Therefore, 3.3 grams of polymer salt was weighed into a 400 ml beaker along with 3.35 grams of potassium chloride. Water was added to a volume of 300 ml. The suspension was stirred and titrated to pH 8.6 using a Metrohm E-536 Potentiograph to record and control the titration. Potassium hydroxide at 0.10N was added. The addition of the base was continued until a constant pH of 8.6 was attained. Approximately one hour was required for each titration because of the slow diffusion of the base into the swollen granules.

The pH of the titration end point was estimated by the Henderson-Hasselbalch equation. The simple form of this equation adequately describes the titration of weak acids with strong bases. Arnold ["The Titration of Polymeric Acids: in Colloid Science Vol. 12, p. 549 (1957)] has estimated the pKa of polyacrylic acid to be 4.5.

$$pKb = pKw - pKa$$
$$= 14 - 4.5$$
$$= 9.5$$

$$pOH = \frac{pKb + p(PAA^-)}{2}$$
$$= \frac{9.5 + \log(1/(PAA^-))}{2}$$

Since 3.3 grams of KPAA represents 1 gram of polyacrylic acid with a repeating unit weight of 72 grams per mole, PAA- was estimated to be at the end point:

$$PAA^- = 1 \text{ gram}/72 \text{ grams per mole}$$
$$= 0.0138 \text{ moles}$$

and $$(PAA^-) = 0.0138 \text{ moles}/0.3 \text{ liter}$$
$$= 0.462 \text{ M}$$

Therefore the pOH at the titration end point is about $$pOH = \frac{9.5 + \log(1/0.0462)}{2}$$
$$= 5.4$$

and $$pH = -14.00 - 5.4$$
$$= 8.6$$

The reslts of this titration are shown in the Table. In the Table, the first three materials are that of Example 5, representing three different runs. The last material is a commercially available superabsorbent.

TABLE

Potassium hydroxide required to reach the titration end point in 1.1 percent suspensions of crosslinked potassium polyacrylate.

| KPAA | KPAA weight of sample in grams | Initial pH | KOH meq/ |
|---|---|---|---|
| 7408-9-6 | 3.3174 | 7.2 | 1.89 |
| 4955-11-5-11 | 3.3136 | 7.2 | 1.61 |
| 4955-1105-16 | 3.3250 | 7.2 | 2.28 |
| ARASORB 720ND | 3.3096 | 6.4 | 7.71 |

As can be seen, by the Titration test employed the Example 5 superabsorbent is substantially neutralized, while the commercial Arasorb 710ND is much less neutralized by the same analytical method. That is significant since Arasorb is the commercial superabsorbent closest to the present invention which has a residual monomer content of only 400 ppm.

It will be understood by those skilled in the art that variations and modifications of the specific embodiments described above may be employed without departing from the spirit and scope of the invention as defined in the appended claims.

We claim:

1. An ionically cross-linked poly (potassium) acrylate superabsorbent composition, which is substantially fully neutralized and water insoluble and which has a low residual monomer content of less than 200 ppm.

2. The superabsorbent of claim 1 which is neutralized to the degree it requires less than 3.0 milliequivalents of 0.1N potassium hydroxide when 3.3 grams of alkali metal polyacrylate are titrated to pH 8.6.

3. An ionically cross-linked poly (alkali metal acrylate) superabsorbent composition comprising a foam product resulting from the process of uniformly reacting acrylic acid, an alkali metal salt of carbonic acid, aluminum acetate, sodium persulfate and water at a temperature of at least 70° C. said composition being substantially neutral and water insoluble and is an alkali metal polyacrylate having a total residual monomer content of both acrylic acid and alkali metal acrylate monomers of less than about 800 ppm.

4. The reaction product of claim 3 wherein said alkali metal salt is comprised of a sodium or potassium salt of carbonic acid.

5. The reaction product of claim 4 wherein said carbonic acid salt is a sodium carbonate salt.

6. The reaction product of claim 5 wherein said salt is potassium carbonate.

7. The superabsorbent composition of claim 3 wherein said total residual monomer content is less than about 200 ppm.

8. An ionically cross-linked poly (alkali metal acrylate) superabsorbent composition comprising the reaction product of about 100 parts of acrylic acid by weight, sufficient parts of an alkali metal salt of carbonic acid to substantially neutralize said acrylic acid, from about 1 to about 7 parts of aluminum acetate, from about 0.2 to about 2 parts of sodium persulfate, and from about 75 to about 175 parts of water reacted in a microwave oven at a temperature of at least 70° C., said reaction product being an alkali metal polyacrylate in the form of a foam having a residual total monomer content of less than about 800 ppm.

9. The reaction product of claim 8 wherein said alkali metal said is comprised of a sodium or potassium salt of carbonic acid.

10. The reaction product of claim 9 wherein said carbonic acid salt is a sodium carbonate salt.

11. The reaction product of claim 9 wherein said salt is potassium carbonate.

12. THe superabsorbent composition of claim 8 wherein the alkali metal salt is potassium and said total residual acrylic acid acrylate monomer content is less than about 200 ppm.

13. A free radical polymerization process for preparing a poly (alkali metal acrylate) using a chemical free-radical initiator, an ionic crosslinking agent, acrylic acid, an alkali metal salt of carbonic acid, and water comprising the steps of: conducting the polymerization reaction by treatment with ultra high frequency waves to obtain a temperature of at least 70° C. for a time sufficient to obtain polymerization whereby the polymerization reaction occurs virtually simultaneously throughout the reaction mixture, thereby obtaining a poly (alkali metal acrylate) having a total residual monomer content below 800 ppm.

14. The process of claim 13 wherein the reaction mixture is acrylic acid, an alkali metal salt of carbonic acid, aluminum acetate, sodium persulfate and water.

15. The process of claim 4 wherein the alkali metal salt of carbonic acid is potassium carbonate and said total residual monomer content is less than about 200 ppm.

16. The process of claim 13 wherein the treatment with ultra high frequency waves is conducted in a microwave oven.

17. The process of claim 13 wherein the treatment with ultra high frequency waves is conducted for at least 1 minute.

18. A product produced by the process of claim 13.

19. A product produced by the process of claim 14.

20. A product produced by the process of claim 15.

* * * * *